(12) United States Patent
Heider et al.

(10) Patent No.: US 7,250,093 B2
(45) Date of Patent: Jul. 31, 2007

(54) METHOD USING A DRY FLUIDISED BED FOR PRODUCING THIN, ABSORBENT SURFACE STRUCTURES

(75) Inventors: Wolfgang Heider, Neustadt (DE); Jürgen Hofmann, Ludwigshafen (DE); Mariola Wanior, Erlensee (DE); Rüdiger Funk, Niedernhausen (DE); Ulrike Licht, Mannheim (DE); Michael Ehle, Ludwigshafen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 192 days.

(21) Appl. No.: 10/467,811

(22) PCT Filed: Feb. 15, 2002

(86) PCT No.: PCT/EP02/01660

§ 371 (c)(1),
(2), (4) Date: Aug. 11, 2003

(87) PCT Pub. No.: WO02/066088

PCT Pub. Date: Aug. 29, 2002

(65) Prior Publication Data

US 2005/0101208 A1 May 12, 2005

(30) Foreign Application Priority Data

Feb. 19, 2001 (DE) .................... 101 07 667

(51) Int. Cl.
*B32B 31/12* (2006.01)
*B32B 31/20* (2006.01)
*B32B 5/16* (2006.01)

(52) U.S. Cl. .......... 156/292; 427/213; 118/303; 604/367

(58) Field of Classification Search ............ None
See application file for complete search history.

(56) References Cited

U.S. PATENT DOCUMENTS

| 4,392,908 | A | * | 7/1983 | Dehnel |
| 4,923,454 | A | * | 5/1990 | Seymour et al. ............ 604/368 |
| 5,436,066 | A | * | 7/1995 | Chen |
| 5,516,585 | A | * | 5/1996 | Young et al. ................ 428/372 |
| 5,549,854 | A | * | 8/1996 | Hulthom et al. |

(Continued)

FOREIGN PATENT DOCUMENTS

CA  2179604  *  6/1995

(Continued)

*Primary Examiner*—Sam Chuan Yao
(74) *Attorney, Agent, or Firm*—Marshall, Gerstein & Borun LLP

(57) ABSTRACT

A process for producing thin absorbent planar structures which may be used in hygiene products such as diapers, incontinence products, wound contact materials or sanitary napkins to absorb body fluids, comprises the steps of:
A) producing a mixture of an adhesive in dispersion form and a particulate absorbent by fluidizing the components,
B) applying the mixture of adhesive and absorbent uniformly to the surface of one side of a first planar backing material,
C) one side of a second planar backing material is applied to the mixture of adhesive and absorbent that is present on the surface of one side of the first planar backing material, so producing a sandwichlike intermediate, and
D) the sandwichlike intermediate is processed to the end product at a temperature of at least 90° C., a pressure of from 4 to 50 bar, and a pressing time of from 0.5 to 5 min.

23 Claims, 1 Drawing Sheet

U.S. PATENT DOCUMENTS 5,582,644 A * 12/1996 Gaddis et al. .............. 118/303
5,756,170 A * 5/1998 Licht et al.
6,066,759 A * 5/2000 Heider et al.
6,150,477 A * 11/2000 Engelhardt et al.

FOREIGN PATENT DOCUMENTS

| | | | |
|---|---|---|---|
| CA | 2345625 | * | 4/2000 |
| EP | 0033235 | * | 8/1981 |
| GB | 2004201 | * | 3/1979 |

* cited by examiner

METHOD USING A DRY FLUIDISED BED FOR PRODUCING THIN, ABSORBENT SURFACE STRUCTURES

CROSS-REFERENCE TO RELATED APPLICATION

This is the U.S. national phase application of International Application No. PCT/EP02/01660, filed Feb. 15, 2002.

BACKGROUND OF THE INVENTION

The invention relates to a process for producing thin absorbent planar structures which may be used in hygiene products such as diapers, incontinence products, wound contact materials or sanitary napkins to absorb body fluids.

Hygiene products or hygiene articles is a term used principally to designate products such as diapers, sanitary napkins, incontinence products or wound contact materials. Depending on their intended use, these hygiene products are suitable for absorbing and storing body fluids such as blood, urine or wound liquid. Whereas, formerly, the active absorbent material contained in the hygiene products consisted predominantly of pure cellulose, modern hygiene products are usually multilayer constructions, with the individual layers assigned specific functions. A distinction is made between a) layers which face the body, b) layers which face the clothing or which lie on the side of the respective hygiene product which is opposite the aforementioned layers, and c) layers located within the interior of the hygiene product.

Layers which are located on the body-facing side of the hygiene product have functions including, firstly, to ensure transport of the body fluids into the interior of said product. Secondly, they are also intended to prevent rewetting; i.e., the body fluids in the interior of the hygiene product in question should not pass back onto the skin. Layers which are located on the clothing-facing side of the hygiene product, in contrast, constitute an impenetrable barrier for the body fluids in both directions. Their principal function, consequently, is to prevent the soiling of clothes or other materials that are in contact with the respective hygiene product.

The most important component of any hygiene product are absorbent planar structures, which are (generally) located in the interior of the hygiene product in question and are also referred to as absorption layers or inner layers. The absorbent planar structures serve to absorb and store the body liquids and include as their principal components a backing material and a swellable substance. The backing material, which serves to distribute the body fluids, is generally constructed of two or more (backing) layers which are bonded adhesively to one another. The swellable substance, which is used to absorb and/or store the body fluids, is incorporated into the backing material and is also termed the absorbent or superabsorbent.

Besides the swelling capacity specific to each individual substance, the fluid absorption capacity of any hygiene product also depends on the amount of absorbent it incorporates. However, it must be borne in mind that only a limited amount of absorbent can be incorporated into the respective hygiene products. The criteria here include not only the stability of the product as a whole but also, in the case of diapers or sanitary napkins in particular, the decrease in wear comfort that accompanies increases in product thickness. Furthermore, especially for relatively large numbers of product units, it is the case that the thinner the product, the easier it is to store and to transport. It should be taken into account here that it is primarily the inner layers, namely those which comprise the absorbent, that contribute to the overall thickness of the hygiene product. Accordingly, the aim is to produce very thin—and hence also lighter—hygiene products and absorbent planar structures which nevertheless possess a high fluid absorption capacity.

The main problem associated with the production of thin absorbent planar structures and, consequently, of hygiene products which are thin overall is the stable fixing of as large as possible an amount of absorbent on or to the backing material. The absorbent is fixed to a first backing layer by means, for example, of an adhesive. The absorbent fixed on the first backing layer is covered in turn by a second, normally identical backing layer. This produces a sandwich-like planar structure in which there is a layer of absorbent between two backing layers. If too much adhesive is used when fixing the absorbent to or between the backing layers, the absorbent may be stably fixed but cannot be packed either very densely or uniformly on the backing. This inevitably produces relatively thick absorbent planar structures; moreover, adhesives tend to be expensive. If, on the other hand, too little adhesive is used, the absorbent is not fixed stably on the backing and the individual backing layers are inadequately bonded to one another as well. As a consequence of this, (some) absorbent crumbles out of the absorbent planar structure which, owing to its deficient absorbent charge, is unusable or at least considerably restricted in its absorption capacity. For the quality of an absorbent planar structure, it is also important how and in what sequence the individual components are connected to one another.

EP-A 0 033 235 describes a process for producing products for absorbing body fluids. There, swellable polymer particles are coated with an adhesive before being fixed on the surface of a water-absorbing backing. The coating of the swellable polymer particles with the adhesive may be effected in a variety of ways. For example, the polymer particles may be carefully mixed with the aqueous solution of an adhesive. A disadvantage here is that the resulting mixture must then be dried thoroughly in order to remove the water introduced with the adhesive from the swellable polymer particles. Alternatively, the swellable polymer particles may be in the form of a slurry in an organic solvent, to which the adhesive is added in solid or dissolved form. This likewise necessitates thorough drying of the resultant mixture. The same applies if the adhesive solution form is sprayed onto the surface of the swellable polymer particles. Alternatively, the adhesive may be incorporated into the swellable polymer particles during their preparation process. This latter process, however, involves a very great deal of synthesis complexity.

All of the coating methods described above, however, are hampered by a further disadvantage, since the mixture of swellable polymer and adhesive must be additionally ground before being applied to the backing material, in order to obtain small particles in powder form which can be distributed on the backing material. In this way it is possible to produce absorbent planar structures containing 100 g/m² swellable polymer based on the surface area of the backing material. The absorbent planar structures are pressed at from 160 to 180° C.

GB-A 2 004 201 describes a further means of fixing absorbent on a backing layer. In this case the absorbent is spread out extensively on the backing and then sprayed with an aqueous solution of an adhesive. A disadvantage of this method is that, through the spray application of the aqueous adhesive solution, the backing layer becomes damp. For this reason, the backing layer must have a considerable minimum thickness, since damp backing layers, especially those based on cellulose, tear very easily and so cannot be processed further.

Absorbent hygiene products comprising at least one layer of a textile material and a swellable natural substance enclosed within it are disclosed in DE-A 43 43 947. Swellable polysaccharides are attached to the backing by means of a divalent crosslinking agent, preferably glyoxal, with the formation of covalent bonds.

Alternatively, formaldehyde-free acrylic adhesives are sprayed onto the backing. In the dry state, however, the hygiene products obtained in this procedure have a considerable total thickness of from to 3 to 7 mm.

BRIEF SUMMARY OF THE INVENTION

It is an object of the present invention to provide absorbent planar structures wherein the absorbent is very tightly packed and stably fixed between the layers of the backing material. At the same time, the absorbent planar structures in the dry state should be extremely thin.

We have found that this object is achieved by a process for producing absorbent planar structure which comprises the following steps:
A) producing a mixture of an adhesive in dispersion form and a particulate absorbent by fluidizing the components,
B) applying the mixture of adhesive and absorbent uniformly to the surface of one side of a first planar backing material,
C) one side of a second planar backing material is applied to the mixture of adhesive and absorbent that is present on the surface of one side of the first planar backing material, so producing a sandwichlike intermediate, and
D) the sandwichlike intermediate is processed to the end product at a temperature of at least 90° C., a pressure of from 4 to 50 bar, and a pressing time of from 0.5 to 5 min.

The advantage of the inventive solution lies in particular in the fact that, owing to the improved process of applying the adhesive to the particles of absorbent, these particles are crosslinked to one another to form a two-dimensional layer and at the same time stable crosslinking to the backing material in the third spatial direction is produced. Accordingly, the particles of absorbent can be packed substantially more tightly to form stable layers, without the risk of particles of absorbent crumbling out of the absorbent planar structure. The stable crosslinking of the layer of particles of absorbent with both the above- and below-lying layers of the backing material produces a significant improvement in the adhesion properties of the individual layers to one another. Owing to the very tightly packed absorbent, thin absorbent planar structures of this kind also perform very highly in terms of their absorption capacity. Consequently, it is possible to produce high-performance absorbent planar structures which nevertheless have a total thickness of only about 1 mm.

The application of a dispersion of the adhesive constitutes a further advantage of the solution. Since the dispersion medium used is absorbed by the particles of absorbent, there is no need for the drying or grinding of the mixture of adhesive and particles of absorbent that is a feature of conventional processes. Because of the relatively small amount of dispersion medium, the absorption capacity of the adhesive-covered absorbent is lessened only slightly in comparison to the absorption capacity of the absorbent without such covering. Moreover, as compared with conventional processes, the amount of adhesive used is relatively small in terms of the amount of absorbent, thereby lowering the production costs.

A further advantage of the inventive solution is the considerable reduction it allows in the thickness of the layers of backing material used. Whereas in conventional adhesive bonding techniques the backing material layers, which generally consist of cellulose (derivatives), are wetted by the applied adhesive and/or the applied absorbent, and so must have a certain minimum thickness, on account of the fact that a damp backing layer tears more easily the thinner it is. With the inventive solution the mixture of adhesive and absorbent is applied in the dry state to the backing layer. Consequently, the thickness of this backing layer may be reduced considerably down to levels of approximately 0.1 mm without any risk of the backing layer tearing in the course of further processing. This makes a considerable contribution to reducing the overall thickness of the absorbent planar structure.

A further advantage of the solution of the invention, which is not to be underestimated, is manifested during the storage of the end product. As a general rule, hygiene products are sold not as individual units but rather in the form of packs containing a large number of units. Thinner hygiene products, accordingly, mean markedly reduced storage capacities, in particular for producers and retailers as well as for the ultimate consumer.

An additional advantage of the inventive solution lies in the adhesives that can be used, which permit the absorbent planar structures to be pressed at temperatures in the range from 100 to 110° C., whereas in conventional pressing techniques the absorbent planar structures must be pressed at temperatures above 160° C. The inventive solution is therefore softer on material and allows energy cost savings to be made.

Step (A) of the process of the invention is illustrated below with reference to a drawing.

DETAILED DESCRIPTION OF THE INVENTION

Figure 1:
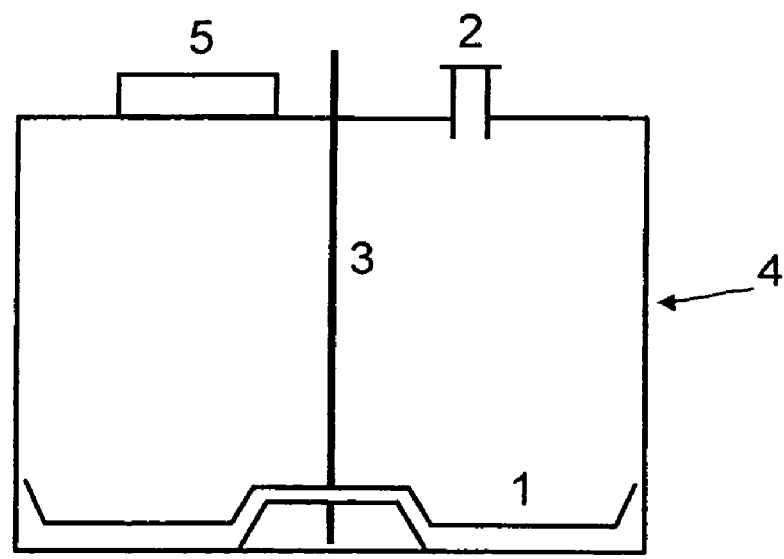
FIG. 1 illustrates a cross section of an apparatus for coating an absorbent with an adhesive.

FIG. 1 depicts a cross section through an apparatus in which an adhesive may be applied to an absorbent. The apparatus essentially comprises a housing 4 in whose interior there is a rotary axle 3 on which in turn a stirrer 1 is mounted. The rotary axle 3 is preferably mounted in the center of the housing 4; the stirrer 1, in a preferred embodiment, is mounted as far as possible at the bottom end of the rotary axle 3 in such a way that the extremities of the stirrer 1 reach as close as possible to the floor and/or the wall of the housing 4. As the stirrer 1 it is possible to use all types of apparatus known to the skilled worker; moreover, the rotary axle 3 may have a suitable actuating drive, preferably an electrical actuating drive, and may if desired be controlled by an arithmetic unit.

Figure 2:
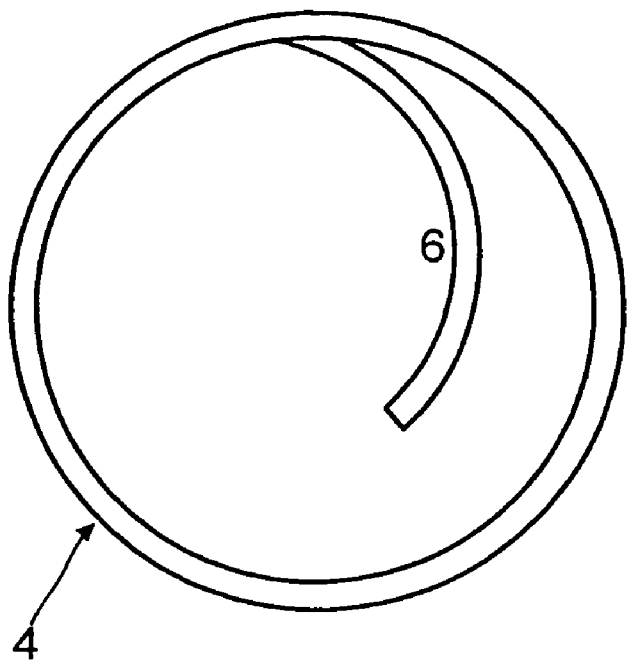
FIG. 2 illustrates a plan view of the apparatus shown in FIG. 1.

The housing 4 is preferably cylindrical. The top of the housing 4 includes a removable lid 5 which is used to introduce and remove substances into and from the interior of the housing 4. The lid 5 may have the customary shapes and aperture sizes; if desired, the lid 5 may also extend over the entire top of the housing 4. Likewise mounted on the top of the housing 4 is an inlet means 2 (hereinafter referred to as inlet 2) which can be used to introduce liquids into the interior of the housing 4. Suitable inlet means 2 include those of which the skilled worker is aware, especially those for introducing dispersions. If desired, the inlet 2 may also be provided in the top third of the side of the housing 4. Additionally, FIG. 2 depicts a plan view of the apparatus described above. From this view it can be seen that mounted in the upper section of the inside of the housing 4 there is at least one apparatus 6 for circulating particle streams (referred to hereinafter as circulating means 6), in particular one or more metal baffle plates. The dimensions in terms of size and thickness and the geometrical forms of the circulation means 6 are known to the skilled worker.

The absorbent is introduced into the interior of the housing 4 by opening the lid 5. The absorbent is preferably in the form of fine dustlike particles but may also be in a coarser, powder or granule form. Particle sizes between 100 and 850 μm are especially suitable. By rotation of the rotary axle 3 and the stirrer 1 connected to it, the absorbent is fluidized in the interior of the housing 4 in such a way that it is distributed over a very large spatial volume and/or so that no particles of the absorbent remain lying on the floor of the housing 4. The circulation means 6 serves here to circulate or influence the particle streams, especially for additional mixing of the fluidized particles or particle streams. When the absorbent is in a fluidized state in the interior of the housing 4, the adhesive is added through the inlet 2. The adhesive is in the form of a dispersion, preferably an aqueous, emulsifier-free dispersion. In one preferred embodiment of the process of the invention the dispersion of the adhesive is sprayed onto the fluidized particles of absorbent. In this case it is important that by means of an appropriate design of the inlet 2 the dispersion of adhesive is sprayed with very fine distribution over the fluidized particles of absorbent.

It is preferred to use dispersions containing from 20 to 50% by weight adhesive, with particular preference from 35 to 45% by weight. The amount of dispersion added through the inlet 2 is guided by the amount of absorbent. Use is made of from 1 to 20% by weight, preferably from 1 to 10% by weight, with particular preference from 4 to 6% by weight of the adhesive, based on the weight of the absorbent.

Following the application of the adhesive to the particles of absorbent, the rotational motion of the stirrer 1 is arrested and the mixture of the absorbent and the adhesive, after it has settled, may be extracted directly for further processing, without additional drying or grinding steps, from the interior of the housing 4. The mixture is preferably in the form of fine particles.

The above-described step A of the process of the invention achieves highly extensive distribution of the adhesive, over a very large number of particles of the absorbent. It is not mandatorily the intention that all particles of the absorbent be fully coated with adhesive. What is preferably desired, is only partial coating or attachment of the adhesive to the individual particles of absorbent, such that the surface of the respective particles is coated with adhesive at one or more points. This may be achieved effectively by means of the above-described weight relations between adhesive, dispersion medium, and absorbent. By adding larger amounts of adhesive, however, it is of course also possible to coat the particles of absorbent with adhesive more extensively or even completely.

Furthermore, it is also possible instead of one absorbent to use mixtures of two or more different kinds of absorbent and/or, instead of an adhesive, to use mixtures of two or more different kinds of adhesives in the process of the invention.

Absorbents which are suitable for the process of the invention for producing thin absorbent planar structures are described in WO 00/22018 and are incorporated by reference into the present invention.

Suitable absorbents include preferably polymers containing structural units which are derived from (meth) acrylic acid or esters thereof or which are obtained by graft (co) polymerization of (meth) acrylic acid or (meth) acrylic esters onto a water-soluble polymer matrix. Examples of suitable graft bases are starch, cellulose, cellulose derivatives, polyvinyl alcohols, polyalkylene oxides, polamines, polyamides or hydrophilic polyesters. Furthermore, suitable polymers preferably include copolymers containing starch and acrylonitrile, vinyl acetate and acrylates or acrylonitrile and acrylamide as their monomer building blocks.

Preferably, the absorbents are in crosslinked form; i.e., the above-described (co)polymers contain at least one unit having at least two double bonds which are incorporated into the polymer network by copolymerization. Particularly suitable for this purpose are methylenebisacrylamide, methylenebismethacrylamide, diacrylates or triacrylates.

Furthermore, in the uncrosslinked or crosslinked absorbents described above, the monomer building blocks containing acid groups that may be present are preferably in salt form with a degree of neutralization of from 50 to 85 mol %, especially in the form of the alkali metal or ammonium salt.

Absorbents suitable with particular preference are those which contain diacrylate-crosslinked poly(meth)acrylic acid and whose monomer building blocks containing acid groups are present in the sodium salt form with a degree of neutralization of from 50 to 85 mol %.

Adhesives suitable for the process of the invention for producing thin absorbent planar structures are all those which develop their adhesive effect within the abovementioned pressure and/or temperature ranges.

Examples of suitable adhesives are the polyurethanes described in EP-A 0 738 750 and incorporated by reference into the present invention. These polyurethanes comprise as monomer building blocks a) at least one polyfunctional isocyanate having from 4 to 30 carbon atoms, b1) from 10 to 100 mol %, based on the total amount of diols, of at least one diol having a molecular weight of from 500 to 5000, at least 80% by weight of the diols b1) having a melting point of from 30 to 100° C. and an enthalpy of fusion in this temperature range of at least 50 J/g, b2) from 0 to 90 mol %, based on the total amount of diols, of at least one diol having a molecular weight of from 60 to 500 g/mol.

Of preferential suitability in this context are polyester polyurethanes, i.e., polyurethanes comprising at least one polyester as diol component and at least one diisocyanate having from 6 to 17 carbon atoms.

Of particularly preferential suitability are polyester polyurethanes containing as monomer building blocks a) tolylene diisocyanate and/or hexamethylene diisocyanate,
b1) polyesters of adipic acid and 1,4-butanediol.

Adhesives of this kind are available commercially in the form, for example, of Luphen® D200A (producer: BASF AG, Ludwigshafen).

The ratio of the monomer building blocks (a) to (b) is preferably approximately 1:1 (in mol %); however, it is also possible to use (significant) excesses of (a) or (b).

If desired, the polyurethanes may be reacted with a PUD salt (an amine containing a sodium carboxylate group). Moreover, it is possible if desired to add water-emulsifiable, polyfunctional isocyanates to the copolymers.

Preferred adhesives for the process of the invention are, furthermore, copolymers obtainable from at least one unsaturated carboxylic acid and at least one olefin.

Of particularly preferential suitability for this purpose are copolymers containing acrylic acid and ethene as monomer building blocks.

Adhesives of this kind are available commercially, in the form, for example, of Poligen® WE3 or Poligen® WE4 (producer: BASF AG, Ludwigshafen).

The above-described adhesives which are used in the process of the invention may be used in the form of a dispersion with or without emulsifier, in particular in the form of an aqueous dispersion which is emulsifier-free.

In step (B) of the process of the invention the mixture of absorbent and adhesive is applied to the surface of one side of a planar backing material. The mixture is distributed uniformly over the surface of the side of the planar backing material so that the individual particles of the mixture are very tightly packed and the resulting layer of particles of the mixture, extending over the surface of one side of the planar backing material, is extremely thin. The individual particles of the mixture can be tightly packed without problems, and it is possible to apply very high coating densities, preferably between 200 and 450 $g/m^2$, based on the surface area of one layer of the backing material, with particular preference between 350 and 400 $g/m^2$. If desired, it is also possible to apply coating densities which are smaller than 200 $g/m^2$.

An important advantage of the process of the invention is to be seen in the fact that the mixture of adhesive and absorbent is applied in the dry state to the backing material, so making it possible to reduce the thickness of the layers of the backing material considerably. The layer thickness of the backing material may readily be reduced to levels of $\leq 0.2$ mm, preferably $\leq 0.1$ mm, without the risk of the backing layer tearing in the course of further processing. If desired, it is also possible readily to coat backing materials having layer thicknesses >0.2 mm with mixtures of adhesive and absorbent.

In the process of the invention, cellulose is a particularly suitable backing material for producing thin absorbent planar structures. Also suitable are cellulose derivatives, other polysaccharides, and further backing materials known to the skilled worker.

In step (C) of the process of the invention, one side of a second planar backing material is applied to the layer of particles of the mixture of adhesive and absorbent, produced in step (B), so that said layer is between the first and second backing material layers. The arrangement comprising the first backing material layer, the layer of particles of the mixture of adhesive and absorbent, and the second backing material layer may be regarded as a sandwichlike intermediate. The two backing layers may differ in their areal dimension, in their thickness and/or in the material used. In one preferred embodiment of the process of the invention, however, the first and second planar backing materials are identical in terms of their areal dimension, their thickness, and the material used. Furthermore, it is possible if desired to attach two or more (optionally different) planar backing material layers, adhesively bonded appropriately to one another, independently of one another to one and/or both sides of the layer of particles of the mixture of adhesive and absorbent in the sandwichlike intermediate. It is likewise possible in turn to insert layers of particles of the mixture of adhesive and absorbent between the respective backing layers.

In step (D) of the process of the invention, the sandwich-like intermediate produced in step (C) is pressed to give the end product. This is done using a press means such as is familiar to the skilled worker, the intermediate being compressed by the press means to preferably 0.3 mm. The pressing time is from 0.5 to 5 min, preferably from 2 to 4 min, with particular preference 3 min. If desired, the pressing time may also last longer than 5 min. The temperature required for pressing should be at least 90° C., with pressing being carried out preferably at from 100 to 110° C.; if desired, the temperature may also be above 110° C. In order to achieve a highly constant pressing temperature, the press means is preheated for an appropriate period of time before the actual pressing operation. The pressing pressure used is from 4 to 50 bar, preferably from 20 to 30 bar, with particular preference 25 bar. If desired, the pressing pressure may also be less than 4 bar or greater than 50 bar.

Accordingly, in step (D) of the process of the invention, an absorbent planar structure is produced from the sandwichlike intermediate, this planar end product being constructed substantially of backing material and absorbent. A feature of this absorbent planar structure is that in the dry, unswollen state it is very thin, preferably 1 mm or less. Moreover, this absorbent planar structure features a very high coating density of absorbent. The coating density is preferably between 200 and 450 $g/m^2$, based on the surface area of a layer of the backing material, with particular preference between 350 and 400 $g/m^2$. If desired, it is also possible without problems to achieve coating densities of less than 200 $g/m^2$.

Both the high coating density and the low thickness of the absorbent planar structure can only be achieved because the adhesive has been applied to the absorbent in accordance with the above-described step (A) of the process of the invention. By virtue of the partial coating of as many particles of the absorbent as possible, these particles adhere both to one another and to the surface of the two layers of the backing material. As a consequence of the very good adhesion properties of the individual layers to one another, it is possible to realize the very thin absorbent planar structures (end product). Moreover, the absorbent planar structures are also notable for a very high coating density (up to 400 $g/m^2$ or more) because the particles of absorbent introduced are bonded so well that they are no longer able to fall out in the form of crumbs from the absorbent planar structure after pressing.

The thin absorbent planar structures produced by the process of the invention find application as components of hygiene products. They are used in particular in hygiene products such as diapers, incontinence products, wound contact materials or sanitary napkins for absorbing body fluids. The body fluids in question include, in particular, blood, urine, and wound fluid. However, the thin absorbent planar structures may also be used in any other hygiene products known to the skilled worker.

It is of course also possible for the adhesive/absorbent mixture produced by the process of the invention to be incorporated into backing materials whose nature is such that thick absorbent planar structures are automatically formed from them.

This applies in particular to incorporation into fluffs, especially into fluffs of cellulose (derivatives).

The examples below are intended to illustrate the invention.

EXAMPLES 1-4

Production of Thin Absorbent Planar Structures

In step (A), 20 g of absorbent are charged to the apparatus. By rotation of the rotary axle 3 and of the stirrer 1 connected to it, the absorbent in the interior of the housing 4 is fluidized in such a way that no particles of the absorbent remain lying on the floor of the housing 4. When the absorbent in the interior of the housing 4 is in the fluidized state, 1 ml of the aqueous, emulsifier-free dispersion of the respective adhesive is added through the inlet 2 into the interior of the housing 4 over a period of 1 minute. The stirrer 1 is subsequently stopped and the mixture of absorbent and adhesive is removed from the apparatus.

| Example | 1 | 2 | 3 | 4 |
|---|---|---|---|---|
| Adhesive used | K1[a] | K2[b] | K2[c] | K3 |
| Solids content of dispersion [%] | 40 | 24–26 | 20–22 | 40 |

The adhesives used comprise essentially:
K1: polyster polyurethanes containing tolylene diisocyanate and polyesters of adipic acid and 1,4-butanediol as monomer building blocks, or
K2: copolymers containing acrylic acid and ethene as monomer building blocks, or
K3: polyester polyurethanes containing hexamethylene diisocyanate and polyesters of adipic and 1,4-butanedoil as monomer building blocks.
[a]The adhesive used is available commercially under the product name Luphen ® D200A (producer: BASF AG, Ludwigshafen).
[b]The adhesive used is available commercially under the product name Poligen ® WE3 (producer: BASF AG, Ludwigshafen).
[c]The adhesive used is available commercially under the product name Poligen ® WE4 (producer: BASF AG, Ludwigshafen).

The adhesives used comprise essentially:

K1: polyester polyurethanes containing tolylene diisocyanate and polyesters of adipic acid and 1,4-butanediol as monomer building blocks, or K2: copolymers containing acrylic acid and ethene as monomer building blocks, or K3: polyester polyurethanes containing hexamethylene diisocyanate and polyesters of adipic acid and 1,4-butanediol as monomer building blocks.

a: The adhesive used is available commerically under the product name Luphen® D200A (producer: BASF AG, Ludwigshafen).

b: The adhesive used is available commerically under the product name Poligen® WE3 (producer: BASF AG, Ludwigshafen).

c: The adhesive used is available commerically under the product name Poligen® WE4 (producer: BASF AG, Ludwigshafen).

The absorbent comprises essentially diacrylate-crosslinked polyacrylic acid, the monomer building blocks containing acid groups being present in sodium salt form with a degree of neutralization of from 50 to 85 mol %.

Step (B) is carried out directly thereafter, the mixture of absorbent and adhesive obtained beforehand being applied uniformly and as a very thin layer to one side of a cellulose cloth (layer thickness: about 0.1 mm; length: 200 mm; width: 200 mm). It is possible to produce coating densities of about 400 g/m$^2$ based on the surface area of one side of the cellulose cloth.

In step (C), one side of a second, identical cellulose cloth is placed onto the surface of the thin layer of the mixture of absorbent and adhesive, so giving the sandwichlike intermediate.

In step (D), the sandwichlike intermediate is pressed to the end product using a laboratory press (producer: IWK; model: HY 1086 (1956)). A heat-resistant sheet is inserted between the two pressing faces and the corresponding sides of the intermediate. After the press has been preheated for 3 minutes, the intermediate is pressed at a temperature of 100° C. (Ex. 1) or 110° C. (Ex. 2-4) and a pressure of 25 bar for a duration of 3 minutes. Using calipers, the distance between the two pressing faces is adjusted to 0.3 mm.

For all 4 examples (Ex. 1-4) stable absorbent planar structures (end product) are produced in this way which have a thickness of 1 mm in the dry state and which are both stable and flexible. In particular it is found that the mixture applied to the cellulose cloth in step (B) of the process of the invention has been fully incorporated into the absorbent planar structure. In other words, under handling or loading under realistic conditions, no absorbent or adhesive/absorbent mixture whatsoever emerges in crumb form from the absorbent planar structure thus produced.

(COMPARATIVE) EXAMPLE 5

Production of Absorbent Planar Structures Using a Foamed Adhesive

The adhesive used (available commercially under the product designation Luphen® D200A (producer: BASF AG, Ludwigshafen)) comprises essentially polyester polyurethanes containing tolylene diisocyanate and polyesters of adipic acid and 1,4-butanediol as monomer building blocks. The adhesive is used in the form of a foam containing approximately 70% by weight of the adhesive. The foam is applied uniformly to one side each of two equal-sized cellulose cloths (layer thickness: about 0.5 mm; length: 200 mm; width: 200 mm) both of which are subsequently coated with the absorbent described in Example 1. Thereafter, the two cellulose cloths with the applied mixture of adhesive and absorbent are dried at 100° C. for 3 minutes. After drying, the two cellulose cloths are placed congruently on top of one another in such a way that the two adhesive/absorbent layers are unified and a sandwichlike intermediate is obtained. Further processing of the sandwichlike intermediate is as in Ex. 1, but with pressing being conducted at a pressure of 50 bar for 5 minutes.

The resulting absorbent planar structure is well bonded and its layer thickness in the dry state after pressing is about 1 mm. A disadvantage, however, is that the coating density of absorbent (about 200 g/m$^2$ based on the surface area of one side of the cellulose cloth) is much lower than in Examples 1-4. Owing to the foam adhesive, the surface of the cellulose cloth cannot be coated with such a high density of absorbent. Moreover, in contrast to Examples 1-4 it is not possible to use cellulose cloths having a layer thickness of about 0.1 mm, since owing to their exposure to the foamed adhesive such cloths tear very readily and are therefore unusable. Consequently, it is possible in general terms to incorporate less absorbent into the absorbent planar structure thus produced in order to be able to obtain a total thickness of approximately 1 mm after the press operation. A further disadvantage is that the absorbent planar structure thus produced, unlike those of Examples 1-4, is very stiff and inflexible.

(COMPARATIVE) EXAMPLE 6

Production of Absorbent Planar Structures Using a Pulverulent Adhesive

The adhesive used is pulverulent oxidized polyethyelene wax (available commercially under the product designation LUWAX® OA5 (producer: BASF AG, Ludwigshafen)) which is first of all mixed with the absorbent described in Example 1.10% by weight of adhesive is used, based on the amount of absorbent.

The mixture of absorbent and adhesive is applied very uniformly to one side of a cellulose cloth (layer thickness: 1 mm; length: 200 mm; width: 200 mm) and is covered with one side of a second, identical cellulose cloth. Further processing is in analogy to Example 5.

The absorbent planar structure produced in this way does not satisfy the requirements in any respect whatsoever. The individual constituents of the absorbent planar structure thus produced are bonded very nonuniformly and incompletely to one another. A large quantity of the absorbent introduced (initial coating density of about 400 g/m$^2$, based on the surface area of one side of a cellulose cloth) falls out of the absorbent planar structure in the form of crumbs when it is handled or loaded under realistic conditions. The coating density of fixedly incorporated absorbent is only about 20% of the amount originally applied and is therefore much lower than in Examples 1-4.

EXAMPLES 7-9

35 Examples 7-9 below indicate that absorbent (AM1+K) to which adhesive has been applied by the process of the invention differs to a negligible extent if at all in terms of its absorbency and swelling properties from untreated absorbent (u–AM1).

EXAMPLE 7

Measurement of the Absorption Capacity (AC)

The absorption capacity, measured in [g/g], shows the maximum absorbency of the respective absorbent.

0.2 g of absorbent is weighed into a teabag measuring 60×85 mm which is subsequently welded. The teabag is then placed in an excess of 0.9% strength by weight sodium chloride solution (at least 0.83 l of sodium chloride solution/g of absorbent). After a swelling time of 60 minutes, the teabag is removed from the sodium chloride solution, excess solution is allowed to drip off, and the swollen teabag is weighed. The absorption capacity is given by the ratio of the weight of the swollen absorbent to the dry absorbent.

EXAMPLE 8

Measurement of the Retention (rot.)

The retention, measured in [g/g], indicates the retention capacity of the respective absorbent under load.

The procedure for the experiment is as in Example 7. However, following the 60-minute swelling time, the teabag is centrifuged for three minutes at an acceleration of 250×g. The teabag is then weighed. The retention is given by the ratio of the weight of the swollen centrifuged absorbent to the dry absorbent.

EXAMPLE 9

Absorption Under Load (AUL)

The absorption under load, measured in [g/g], indicates the extent of the swelling capacity of the respective absorbent in the face of a force acting from externally. The procedure for the experiment is as in Example 7. However, additional weights are placed on the teabag, exerting a load of 0.3 or 0.7 psi on the respective absorbent.

EVALUATION of EXAMPLES 7-9

| Example | 7 (AC) | 8 (rot.) | 9A (AUL/0.3 psi) | 9B (AUL/0.7 psi) |
|---|---|---|---|---|
| AM1 + K | 42.8 | 26.9 | 27.8 | 21.1 |
| u-AM1 | 43.8 | 28.8 | 27.0 | 20.7 |

The absorbent used (AM1) comprises essentially diacrylate-crosslinked polyacrylic acid, the monomer building blocks containing acid groups being present in the sodium salt form with a degree of neutralization of from 50 to 85 mol %. The adhesive used (K/available commercially under the product designation Luphen® D200A (producer: BASF AG, Ludwigshafen)) comprises essentially polyester polyurethanes containing tolylene diisocyanate and polyester of adipic acid and 1,4-butanediol as monomer building blocks.

Examples 7-9 therefore show that the incorporation of the adhesive-bearing absorbent into absorbent planar structures by the process of the invention does not lead to any notable adverse changes in respect of the absorbency or swelling properties of the absorbent used.

List of Reference Numerals

1 Stirrer
2 Inlet means
3 Rotary axle
4 Housing
5 Lid
6 Means for circulating particle streams

We claim
1. A process for producing an absorbent planar structure in which an adhesive and an absorbent are applied to a backing material, comprising
 (a) producing a mixture consisting of an adhesive in dispersion form and a particulate absorbent by fluidizing the adhesive and the absorbent, said absorbent selected from the group consisting of:
  i) a polymer containing structural units derived from a (meth)acrylic acid, or salt or ester thereof,
  ii) a polymer obtained by graft (co)polymerization of a (meth)acrylic acid or a (meth)acrylic ester onto a water-soluble polymer matrix, and
  iii) a copolymer containing starch and acrylonitrile, vinyl acetate and an acrylate, or acrylonitrile and acrylamide as its monomer building blocks,
 (b) applying the mixture of step (a) uniformly to a surface of one side of a first planar backing material,
 (c) applying one side of a second planar backing material to the mixture of step (a) that is present on the surface of one side of the first planar backing material to produce a sandwich-like intermediate, and
 (d) processing the sandwich-like intermediate at a temperature of at least 90° C., a pressure of from 4 to 50 bar, and a pressing time of from 0.5 to 5 minutes to provide the absorbent planar structure.
2. The process of claim 1 wherein the adhesive is in the form of an aqueous, emulsifier-free dispersion.

3. The process of claim 1 wherein 1% to 20%, by weight, of the adhesive is used, based on the amount of the absorbent.

4. The process of claim 1 wherein 1% to 10%, by weight, of the adhesive is used, based on the amount of the absorbent.

5. The process of claim 1 wherein the absorbent comprises a diacrylate-crosslinked poly(meth)acrylic acid, in the sodium salt form and having a degree of neutralization of 50 to 85 mol %.

6. The process of claim 1 wherein the adhesive comprises:
    (a) a polyester polyurethane having monomer building blocks
        (a1) tolylene diisocyanate, hexamethylene diisocyanate, or a mixture thereof, and
        (a2) a polyester of adipic acid and 1,4-butanediol; or
    (b) a copolymer containing acrylic acid and ethene as monomer building blocks.

7. The process of claim 1 wherein the backing material comprises cellulose.

8. The process of claim 1 wherein the first backing material has a layer thickness of less than or equal to 0.2 mm.

9. The process of claim 1 wherein the first backing material has a layer thickness of less than or equal to 0.1 mm.

10. The process of claim 1 wherein the sandwich-like intermediate is pressed at a temperature of 100° C. to 110° C.

11. The process of claim 1 wherein the sandwich-like intermediate is pressed at a pressure of 20 to 30 bar.

12. The process of claim 1 wherein the sandwich-like intermediate is pressed in a pressing time of 2 to 4 minutes.

13. The process of claim 1 wherein the absorbent planar structure contains 350 to 400 g/m$_2$ of the absorbent, based on the surface area of one side of the backing material.

14. The process of claim 1 wherein the absorbent planar structure has a thickness of less than or equal to 1 mm.

15. A method of absorbing a body fluid comprising ccntacting forming a thin absorbent planar structure in process of claim 1, and contacting the body fluid with the thin absorbent planar structure.

16. The process of claim 1 wherein the second backing material has a layer thickness of less than or equal to 0.2 mm.

17. The process of claim 1 wherein the second backing material has a layer thickness of less than or equal to 0.1 mm.

18. The process of claim 1 wherein the first backing material and the second backing material are identical in areal dimension and thickness.

19. The process of claim 1 wherein the first backing material and the second backing material differ in areal dimension or thickness, or both.

20. The process of claim 1 wherein the first backing material and the second backing material comprise an dentical material of construction.

21. The process of claim 1 wherein the absorbent comprises a mixture of two or more absorbents.

22. The process of claim 1 wherein the adhesive comprises a mixture of two or more adhesives.

23. A process for producing an absorbent planar structure in which an adhesive and an absorbent are applied to a backing material, comprising
    (a) producing a mixture consisting of an adhesive in dispersion form and a particulate absorbent by fluidizing the adhesive and the absorbent, said absorbent selected from the group consisting of:
        i) a polymer containing structural units derived from a (meth)acrylic acid, or salt or ester thereof,
        ii) a polymer obtained by graft (co)polymerization of a (meth)acrylic acid or a (meth)acrylic ester onto a water-soluble polymer matrix, arid
        iii) a copolymer containing starch and acrylonitrile, vinyl acetate and an acrylate, or acrylonitrile and acrylarmide as its monomer building blocks,
    (b) applying the mixture of step (a) uniformly to a surface of one side of a first planar backing material,
    (c) applying one side of a second planar backing material to the mixture of step (a) that is present on the surface of one side of the first planar backing material to produce a sandwich-like intermediate, and
    (d) processing the sandwich-like intermediate at a temperature of at least 90° C., a pressure of from 4 to 50 bar, and a pressing time of from 0.5 to 5 minutes to provide the absorbent planar structure,
    wherein the absorbent planar structure contains 200 to 450 g/m$^2$ of the absorbent, based on the surface area of one side of the backing material.

* * * * *

UNITED STATES PATENT AND TRADEMARK OFFICE
CERTIFICATE OF CORRECTION

PATENT NO. : 7,250,093 B2
APPLICATION NO. : 10/467811
DATED : July 31, 2007
INVENTOR(S) : Wolfgang Heider et al.

Page 1 of 1

It is certified that error appears in the above-identified patent and that said Letters Patent is hereby corrected as shown below:

On the Title Page:

At Item (30), "101 07 667" should be -- 10107667.3 --.

In the Claims:

At Column 13, line 35, claim 13, "g/m$_2$" should be -- g/m$^2$ --.

At Column 13, line 40, claim 15, "ccntacting forming" should be -- forming --.

At Column 13, lines 40-41, claim 15, "in process" should be -- in a process --.

At Column 14, lines 9-10, claim 20, "dentical" should be -- identical --.

Signed and Sealed this

Eighteenth Day of December, 2007

JON W. DUDAS
*Director of the United States Patent and Trademark Office*